United States Patent [19]
Woo et al.

[11] Patent Number: 6,039,981
[45] Date of Patent: Mar. 21, 2000

[54] ANTIFUNGAL ORAL COMPOSITION CONTAINING ITRACONAZOLE AND PROCESS FOR PREPARING SAME

[75] Inventors: Jong-Soo Woo, Suwon; Hong-Gi Yi, Kyungki-do, both of Rep. of Korea

[73] Assignee: Hanmi Pharm. Co. Ltd., Kyungki-do, Rep. of Korea

[21] Appl. No.: 09/411,510

[22] Filed: Oct. 4, 1999

[30] Foreign Application Priority Data

Jun. 16, 1999 [KR] Rep. of Korea ................ 99-22472

[51] Int. Cl.⁷ .................... A61K 33/42; A61K 31/495
[52] U.S. Cl. ............................... 424/601; 514/252
[58] Field of Search ................ 424/601; 514/252

[56] References Cited

U.S. PATENT DOCUMENTS 5,474,997  12/1995  Gray et al. ............... 514/252
5,750,147  5/1998   Kantor .................... 424/491

*Primary Examiner*—Raymond Henley, III
*Attorney, Agent, or Firm*—Friedman & Siegelbaum LLP

[57] ABSTRACT

An antifungal oral composition comprising a fused mixture of itraconazole and phosphoric acid provides a high in vivo bioavailability of itraconazole.

5 Claims, 1 Drawing Sheet

ANTIFUNGAL ORAL COMPOSITION CONTAINING ITRACONAZOLE AND PROCESS FOR PREPARING SAME

FIELD OF THE INVENTION

The present invention relates to an oral composition of itraconazole having improved itraconazole bioavailability, and a process for the preparation thereof.

BACKGROUND OF THE INVENTION

Itraconazole, a triazole compound, is known to have excellent antifungal activity. However, the bioavailability of orally administered itraconazole is very low because it has a very low solubility of less than 1 µg/ml in water and it remains unionized in the gastric juice due to its pKa value of 3.7. Further, it is known that the degree of bioavailability of orally administered itraconazole varies widely among individuals and depends on other factors such ingested foods.

PCT International Publication No. WO 85/02767 and U.S. Pat. No. 4,764,604 teach a method for increasing the solubility of itraconazole by employing a cyclodextrin inclusion compound of itraconazole. However, this method has the problems that the incremental increase in the itraconazole solubility is only marginal and various complicated preparative procedures are required.

Recently, PCT International Publication No. WO 94/05263 discloses a coated bead preparation, wherein a core made of pharmaceutically inert or neutral sucrose, dextrine, starch and the like is coated with a mixture of itraconazole and a hydrophilic polymer and, then, the resulting bead is coated again with a polymer, e.g., polyethylene glycol. Such a coated bead preparation is commercially available from Janssen Pharmaceutica(Beerse, Belgium) under the trade name of Sporanox® capsule. However, the manufacturing process of the above preparation is very complicated due to the fact the beads having an average size of only 600 to 700 µm tend to undergo agglomeration during the manufacturing process.

PCT International Publication No. WO 97/44014 teaches a solid dispersion of itraconazole in a water-soluble polymer, which is prepared by subjecting a mixture of itraconazole and the water-soluble polymer to a melt-extrusion process at a temperature ranging from 245° C. to 265° C. This solid dispersion is described to have an improved bioavailability of itraconazole which is not influenced by ingested foods, and it is commercially available from Janssen Pharmaceutica(Beerse, Belgium) under the trade name of Sporanox® tablet. However, the manufacturing process of the solid dispersion is hampered by a number of difficulties in controlling various process variables, and the in vivo bioavailability of itraconazole achievable with the above dispersion is still low.

Accordingly, there has existed a need to develop an oral composition having improved in vivo bioavailability of itraconazole.

SUMMARY OF THE INVENTION

It is, therefore, an object of the present invention to provide an improved oral composition comprising itraconazole.

Another object of the present invention is to provide a process for preparing said oral composition.

In accordance with one aspect of the present invention, there is provided an antifungal composition for oral administration comprising a fused mixture of itraconazole and phosphoric acid, a pharmaceutically acceptable carrier and a surfactant.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1:
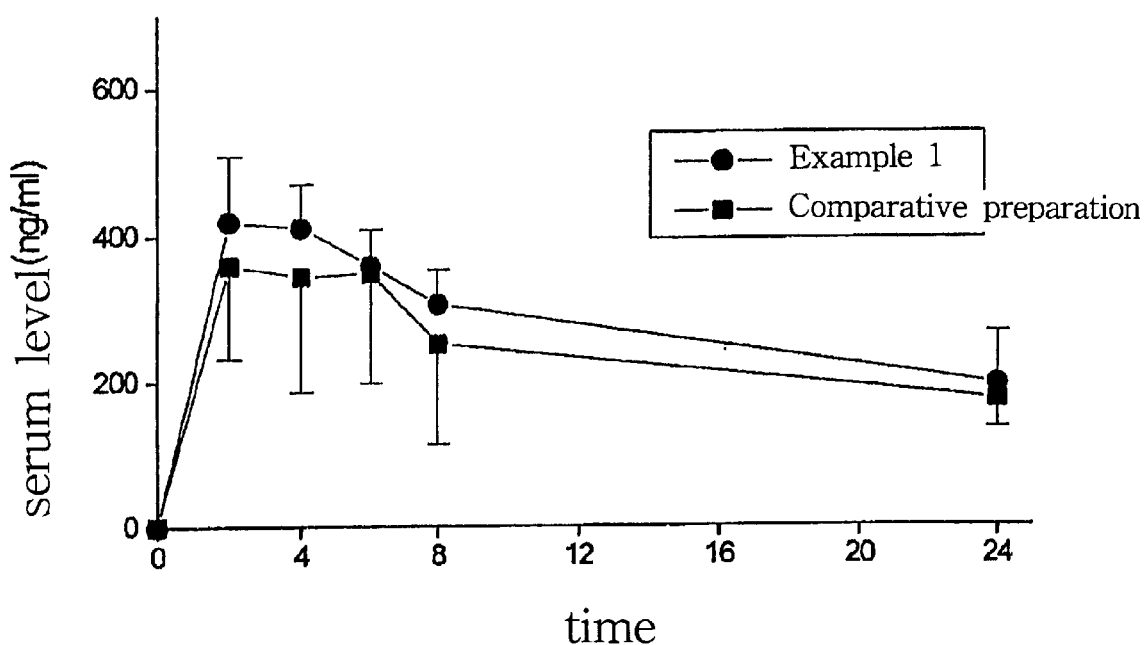
FIG. 1 shows the bioavailabilities of the inventive itraconazole preparation and a commercially available itraconazole preparation.

Throughout this specification, a solid obtained by the steps of fusing itraconazole with phosphoric acid to form a melt and cooling the melt is designated a fused mixture of itraconazole and phosphoric acid. Such a mixture has a melting point which is much lower than that of itraconazole, and the dissolution of itraconazole from said mixture into an aqueous solution is greatly enhanced as compared with solid itraconazole, with a consequential increase of the in vivo bioavailability of itraconazole.

The weight ratio of itraconazole and phosphoric acid in the fused mixture of the present invention is in the range of 1:0.1 to 1:10, preferably, 1:0.5 to 1:5.

The inventive composition comprising a fused mixture of itraconazole and phosphoric acid may contain a pharmaceutically acceptable carrier such as lactose, dextrin, starch, microcrystalline cellulose, hydroxypropyl methylcellulose, hydroxypropyl cellulose, hydroxyethyl cellulose, ethyl cellulose, methyl cellulose, polyethylene glycol, silicon dioxide, hydrotalcite, aluminum magnesium silicate, aluminum hydroxide, aluminum silicate, magnesium aluminum metasilicate, bentonite and a mixture thereof.

The antifungal oral composition of the present invention may further comprise a surfactant which promotes the wetting of the fused mixture of itraconazole and phosphoric acid in a aqueous medium. Representative examples of the surfactant include:

(1) polyoxyethylene glycolated natural or hydrogenated vegetable oils such as polyoxyethylene glycolated natural or hydrogenated castor oil (Cremophor®, BASF), (2) polyoxyethylene-sorbitan-fatty acid esters wherein fatty acid is mono- or tri-lauric, palmitic, stearic or oleic acid (Tween®, ICI), (3) polyoxyethylene fatty acid esters such as polyoxyethylene stearic acid ester (Myrj, ICI), (4) polyoxyethylene-polyoxypropylene block copolymer (Poloxamer®, BASF), (5) sodium dioctyl sulfosuccinate or sodium lauryl sulfate, (6) phospholipids, (7) propylene glycol mono- or di-fatty acid esters such as propylene glycol dicaprylate, propylene glycol dilaurate, propylene glycol isostearate, propylene glycol laurate, propylene glycol ricinoleate, propylene glycol caprylic-capric acid diester(Miglyol® 840, Hüls), (8) trans-esterification products of natural vegetable oil triglycerides and polyalkylene polyols(Labrafil® M, Gattefosse), (9) mono-, di- or mono/di-glycerides such as caprylic/capric acid mono- and di-glycerides(Imwitor®, Hüls), and

(10) sorbitan fatty acid esters such as sorbitan monolauryl, sorbitan monopalmityl and sorbitan monostearyl esters(Span®, ICI).

Among the above-mentioned surfactants, polyoxyethylene glycolated natural or hydrogenated vegetable oils, polyoxyethylene-sorbitan-fatty acid esters, and polyoxyethylene-polyoxypropylene block copolymer are preferably used in the present invention.

Further, in accordance with another aspect of the present invention, there is provided a process for preparing the inventive composition comprising (a) mixing itraconazole and phosphoric acid, (b) heating the mixture to a temperature ranging from 100 to 170° C. to obtain a homogeneous melt mixture, (c) adding a pharmaceutically acceptable carrier and a surfactant thereto, (d) cooling the resulting mixture to obtain a solid, and (e) pulverizing the solid.

Alternatively, the inventive composition may be prepared by employing an organic solvent, e.g., ethanol, methylene chloride and chloroform. Specifically, itraconazole is mixed with phosphoric acid and a small amount of an organic solvent is added to the resulting mixture to obtain a solution. Subsequently, a pharmaceutically acceptable carrier and a surfactant are added thereto, and the resulting solution is heated to vapourize the solvent and then cooled to obtain a solid, which is then pulverized.

The pharmaceutical composition of the present invention may be formulated into various pharmaceutical preparations, e.g., powder, granule, tablet, coated preparation and liquid preparation, in accordance with any of the conventional procedures. For instance, a hard capsule may be prepared by adding a lubricant and other pharmaceutical additives to the pharmaceutical composition, processing the mixture into a powder or granules and filling the powder or granules into a hard gelatin capsule; a tablet, by adding a suitable additive to the pharmaceutical composition and tableting the mixture; a liquid preparation, by dissolving the pharmaceutical composition in water; and a coated preparation, by coating a solution of the pharmaceutical composition on a sugar bead such as Non-pareil®(Edward Mendell Co., UK).

As described above, the inventive composition comprising a fused mixture of itraconazole and phosphoric acid gives a remarkably high in vivo bioavailability of itraconazole. Further, the inventive method for the preparation of the inventive antifungal composition comprising itraconazole has an advantage over prior art methods in that it is a lower temperature process having a high productivity.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1
Preparation of Hard Capsule

A hard capsule was prepared using the following ingredients:

|  | Quantity (mg/capsule) |
|---|---|
| Itraconazole | 100 |
| Phosphoric acid 85% | 150 |
| Poloxamer ® 407 | 30 |
| Cremophor ® RH40 | 10 |
| Hydroxypropyl methylcellulose | 20 |
| Hydrotalcite | 70 |
| Silicon dioxide | 20 |

Itraconazole and phosphoric acid were mixed and the mixture was heated to 160° C. to obtain a fused melt. Other ingredients except silicon dioxide were added thereto while the mixture was allowed to cool. Then, the resulting mixture was cooled to room temperature to obtain a fused solid. The solid was mixed with silicon dioxide, pulverized and filled into a hard gelatin capsule.

EXAMPLE 2
Preparation of Hard Capsule

A hard capsule was prepared by the procedure of Example 1 using the following ingredients:

|  | Quantity (mg/capsule) |
|---|---|
| Itraconazole | 100 |
| Phosphoric acid 85% | 100 |
| Poloxamer ® 407 | 30 |
| Tween ® 80 | 10 |
| Hydroxypropyl methylcellulose | 20 |
| Hydrotalcite | 70 |
| Silicon dioxide | 20 |

EXAMPLE 3
Preparation of Hard Capsule

A hard capsule was prepared by the procedure of Example 1 using the following ingredients:

|  | Quantity (mg/capsule) |
|---|---|
| Itraconazole | 100 |
| Phosphoric acid 85% | 100 |
| Poloxamer ® 407 | 30 |
| Cremophor ® RH40 | 10 |
| Hydrotalcite | 100 |
| Silicon dioxide | 20 |

EXAMPLE 4
Preparation of Hard Capsule

A hard capsule was prepared by the procedure of Example 1 using the following ingredients:

|  | Quantity (mg/capsule) |
|---|---|
| Itraconazole | 100 |
| Phosphoric acid 85% | 150 |
| Tween ® 80 | 20 |
| Cremophor ® RH40 | 10 |
| Hydrotalcite | 70 |
| Silicon dioxide | 20 |

EXAMPLE 5
Preparation of Hard Capsule

A hard capsule was prepared by the procedure of Example 1 using the following ingredients:

| | Quantity (mg/capsule) |
|---|---|
| Itraconazole | 100 |
| Phosphoric acid 85% | 50 |
| Poloxamer ® 407 | 40 |
| Cremophor ® RH40 | 20 |
| Hydrotalcite | 70 |
| Silicon dioxide | 20 |

EXAMPLE 6
Preparation of Hard Capsule

A hard capsule was prepared by the procedure of Example 1 using the following ingredients:

| | Quantity (mg/capsule) |
|---|---|
| Itraconazole | 100 |
| Phosphoric acid 85% | 150 |
| Poloxamer ® 407 | 30 |
| Cremophor ® RH40 | 10 |
| Polyethylene glycol (PEG) 20000 | 150 |
| Silicon dioxide | 20 |

EXAMPLE 7
Preparation of Hard Capsule

A hard capsule was prepared using the following ingredients:

| | Quantity (mg/capsule) |
|---|---|
| Itraconazole | 100 |
| Phosphoric acid 85% | 100 |
| Ethanol | 500 |
| Poloxamer ® 407 | 100 |
| Cremophor ® RH40 | 50 |
| Polyethylene glycol (PEG) 20000 | 200 |

Itraconazole and phosphoric acid were mixed, and ethanol was added to the mixture to obtain a solution. Other ingredients were added thereto, and the resulting solution was heated to 100° C. to vapourize the ethanol and then cooled to room temperature to obtain a solid. The solid was pulverized and filled into a hard gelatin capsule.

EXAMPLE 8
Preparation of Hard Capsule Containing Coated Beads

A hard capsule containing coated beads was prepared using the following ingredients:

| | Quantity (mg/capsule) |
|---|---|
| Itraconazole | 100 |
| Phosphoric acid 85% | 200 |
| Ethanol | 500 |
| Polyethylene glycol (PEG) 20000 | 100 |
| Cremophor ® PH40 | 20 |
| Sugar beads | 400 |

A mixture containing other ingredients except ethanol was prepared by the procedure of Example 7, wherein it contained one half portion of PEG 20000. The mixture was evenly coated on sugar beads, followed by coating thereon the remaining portion of PEG 20000. The coated sugar beads thus obtained were filled into a hard gelatin capsule.

Comparative Example
Preparation of Hard Capsule

A hard capsule was prepared by the procedure of Example 1, except that phosphoric acid was not employed, using the following ingredients:

| | Quantity (mg/capsule) |
|---|---|
| Itraconazole | 100 |
| Poloxamer ® 407 | 30 |
| Cremophor ® RH40 | 10 |
| Hydroxypropyl methylcellulose | 20 |
| Hydrotalcite | 70 |
| Silicon dioxide | 20 |

Test Example 1
Dissolution Test

Dissolution rates of itraconazole were determined for the inventive preparations of Examples 1 to 3; the preparation of Comparative Example; Sporanox® capsule; and Sporanox® tablet(Janssen Korea), in accordance with the dissolution test method II(paddle method) described in the General Tests chapter of Korean Pharmacopoeia under the conditions listed below:

Test apparatus: Erweka DT80(Erweka, Germany)
Test solutions: 900 ml of 0.1 N Hcl
Temperature of test solutions: 37±0.5° C.
Rotation speed: 100±4 rpm
Analytical method: liquid chromatography
    column: Cosmosil C18(150 mm×4.6 mm; Nacalai tesque, Japan)
    mobile phase: acetonitrile/phosphate buffer(Ph 7.0)= 60:40
    flow rate: 1.2 ml/min.
    detector: UV 255 nm
    injection volume: 10 $\mu$l The amount of dissolved itraconazole is represented by the cumulative amount of itraconazole eluted in 45 min. and the results are shown in Table 1.

TABLE 1

| Sample | Example 1 | Example 2 | Example 3 | Comparative Example | Sporanox ® capsule | Sporanox ® tablet |
|---|---|---|---|---|---|---|
| Dissolved amount (45 min.) | 94% | 91% | 96% | 15% | 50% | 92% |

As can be seen in Table 1, the preparations of Examples 1 to 3 exhibit remarkedly higher amounts of itraconazole dissolved than those of Comparative Example and Sporanox® capsule. This result proves that the solubilization of itraconazole in water is greatly enhanced by using the inventive fused mixture of itraconazole and phosphoric acid.

Further, although preparation of Sporanox® tablet shows a high level of dissolved itraconazole similar to those of Examples 1 to 3, the manufacturing process of the inventive preparations is much simpler and has a higher productivity than that of Sporanox® tablet. Further, the in vivo bioavailability of itraconazole in Sporanox® tablet is significantly lower as compared with the inventive composition, as shown in Test Example 2.

Test Example 2

In Vivo Absorption Test

In order to investigate the bioavailability of itraconazole contained in the inventive preparations, in vivo absorption tests were carried out as follows.

Thirty 14 or 15 week-old male Sprague-Dawly rats each weighing about 300 g were fasted for over 48 hours while they were allowed free access to water, and then divided into two groups each containing 10 rats.

The two groups of rats were orally administered with the inventive preparation of Examples 1 and Sporanox® tablet, respectively, in a dose of 20 mg itraconazole/kg body weight of the rat. Blood samples were taken directly from the hearts of the rats before the administration and after 2, 4, 6, 8 and 24 hours from the administration, and sera were separated therefrom.

Added to 500 μl each of the serum samples were 50 μl of an internal standard solution(methanol solution containing 500 μg/ml of nitrate econazole) and 200 μl of 1 M carbonate buffer(Ph 10.0). 7 ml of an extraction solvent(n-heptane:isoamylalchol=9:1) was added thereto and the resulting mixture was shaken at 80 rpm for 5 min. to obtain an extract. The extract was centrifuged at 3,000 rpm for 10 min. and the solvent was evaporated at 50° C. under a nitrogen atmosphere. To the resulting residue was added 200 μl of 0.05% triethylamine solution of 65% aqueous acetonitrile and the mixture was subjected to HPLC under the following conditions:

column: Inertsil ODS2(250×4.6 mm, 5 μm; GL science, Japan)

mobile phase: 65% aqueous acetonitrile solution containing 0.05% triethylamine detector: UV 258 nm flow rate: 1.2 ml/min.

injection volume: 100 μl

The result in FIG. 1 shows that the bioavailability of itraconazole observed for the inventive preparation is much higher as compared to Sporanox® tablet.

While the invention has been described with respect to the above specific embodiments, it should be recognized that various modifications and changes may be made to the invention by those skilled in the art which also fall within the scope of the invention as defined by the appended claims.

What is claimed is:

1. An antifungal composition for oral administration comprising a fused mixture of itraconazole and phosphoric acid, a pharmaceutically acceptable carrier and a surfactant.

2. The antifungal composition of claim 1, wherein the weight ratio of itraconazole and phosphoric acid in the fused mixture ranges from 1:0.1 to 1:10.

3. The antifungal composition of claim 1, wherein the pharmaceutically acceptable carrier is selected from the group consisting of: lactose, dextrin, starch, microcrystalline cellulose, hydroxypropyl methylcellulose, hydroxypropyl cellulose, hydroxyethyl cellulose, ethyl cellulose, methyl cellulose, polyethylene glycol, silicon dioxide, hydrotalcite, aluminum magnesium silicate, aluminum hydroxide, aluminum silicate, magnesium aluminum metasilicate, bentonite and a mixture thereof.

4. The antifungal composition of claim 1, wherein the surfactant is selected from the group consisting of: polyoxyethylene glycolated natural or hydrogenated vegetable oils, polyoxyethylene-sorbitan-fatty acid esters, polyoxyethylene fatty acid esters, polyoxyethylene-polyoxypropylene block copolymer, sodium dioctyl sulfosuccinate, sodium lauryl sulfate, phospholipids, propylene glycol mono- or di-fatty acid esters, trans-esterification products of natural vegetable oil triglycerides and polyalkylene polyols, monoglycerides, diglycerides, mono/di-glycerides and sorbitan fatty acid esters.

5. A process for preparing the antifungal composition of claim 1 comprising:

(a) mixing itraconazole and phosphoric acid, (b) heating the mixture to a temperature ranging from 100 to 170° C. to obtained a homogeneous melt mixture, (c) adding the pharmaceutically acceptable carrier and surfactant thereto, (d) cooling the melt mixture to obtain a solid, and (e) pulverizing the solid.

* * * * *